United States Patent
Baures et al.

(10) Patent No.: US 8,314,231 B2
(45) Date of Patent: Nov. 20, 2012

(54) SYSTEMS, COMPOSITIONS, AND/OR METHODS FOR DEPOLYMERIZING CELLULOSE AND/OR STARCH

(75) Inventors: Marc A. Baures, Ettrick, WI (US); Charles Alfred Krier, Brookfield, WI (US); Henry W. Cox, Blacksburg, VA (US)

(73) Assignee: Hydrite Chemical Co., Brookfield, WI (US)

( * ) Notice: Subject to any disclaimer, the term of this patent is extended or adjusted under 35 U.S.C. 154(b) by 130 days.

(21) Appl. No.: 12/599,205

(22) PCT Filed: May 1, 2008

(86) PCT No.: PCT/US2008/062176
§ 371 (c)(1),
(2), (4) Date: Aug. 17, 2010

(87) PCT Pub. No.: WO2008/137517
PCT Pub. Date: Nov. 13, 2008

(65) Prior Publication Data
US 2010/0311139 A1 Dec. 9, 2010

Related U.S. Application Data

(60) Provisional application No. 60/916,376, filed on May 7, 2007.

(51) Int. Cl.
*C07H 1/00* (2006.01)
*C07H 3/00* (2006.01)
*C08B 37/00* (2006.01)

(52) U.S. Cl. ...................................... 536/124
(58) Field of Classification Search ................ None
See application file for complete search history.

(56) References Cited

U.S. PATENT DOCUMENTS

| | | | |
|---|---|---|---|
| 2,920,011 | A | 1/1960 | Eilers, Jr. |
| 3,655,644 | A | 4/1972 | Durand |
| 3,865,685 | A | 2/1975 | Hebbel et al. |
| 3,975,206 | A | 8/1976 | Lotzgesell et al. |
| 4,056,400 | A | 11/1977 | Diamantoglau et al. |
| 4,222,819 | A | 9/1980 | Fossum et al. |
| 4,314,854 | A | 2/1982 | Takagi |
| 4,436,586 | A | 3/1984 | Elmore |
| 4,462,864 | A | 7/1984 | Carles et al. |
| 4,649,113 | A | 3/1987 | Gould |
| 4,661,205 | A | 4/1987 | Ow et al. |
| 4,806,475 | A | 2/1989 | Gould |
| 4,838,944 | A | 6/1989 | Kruger |
| 5,188,673 | A | 2/1993 | Clausen et al. |
| 5,726,046 | A | 3/1998 | Farone et al. |
| 5,833,755 | A | 11/1998 | Schlom et al. |
| 5,929,012 | A | 7/1999 | Del Duca et al. |
| 6,007,636 | A | 12/1999 | Lightner |
| 6,702,921 | B2 | 3/2004 | Duggirala et al. |
| 6,780,306 | B2 | 8/2004 | Schlager et al. |
| 6,960,330 | B1 | 11/2005 | Cox, Jr. |
| 6,998,099 | B2 | 2/2006 | Hesse et al. |
| 7,033,481 | B1 | 4/2006 | Schlager et al. |
| 7,078,370 | B2 | 7/2006 | Crews |
| 7,101,691 | B2 | 9/2006 | Kinley et al. |
| 2005/0039270 | A1 | 2/2005 | Legrand et al. |
| 2006/0169595 | A1 | 8/2006 | Schlager et al. |
| 2006/0180463 | A1 | 8/2006 | Schlager et al. |

FOREIGN PATENT DOCUMENTS

| | | |
|---|---|---|
| CA | 2300807 | 9/2000 |
| WO | 01/27069 | 4/2001 |
| WO | 2004/007559 | 1/2004 |

OTHER PUBLICATIONS

Ramo. Hydrogen peroxide—metals—chelating agents; interactions and analytical techniques, Academic dissertation, Apr. 25, 2003, Chapter 3, pp. 18-25.*
Guay et al., "Mechanisms of Oxidative Degradation of Carbohydrates During Oxygen Delignification III. Reaction of Photochemically Generated Hydroxyl Radicals with 1,5-Anhydrocellobiotol and Cellulose," Journal of Pulp and Paper Science, 28:7, 2002.
Narendranath, N.V., et al. Urea Hydrogen Peroxide Reduces the Numbers of Lactobacilli, Nourishes Yeast, and Leaves No Residue in the Ethanol Fermentation, Applied and Environmental Microbiology, Oct. 2000, p. 4187-4192, 66:10.
Petit, et al. Free-Radical Depolymerization with Metallic Catalysts of an Exopolysaccharide Produced by a Bacterium Isolated from a Deep-Sea Hydrothermal Vent Polychaete annelid, 2006, Carbohydrate Polymers, vol. 64, p. 597-602.
International Search Report and Written Opinion under date of Mailing of Aug. 6, 2008, corresponding to PCT/US08/62176.
Guay et al., Mechanisms of Oxidative Degradation of Carbohydrates During Oxygen Delignification. I. Reaction of Methyl b-D-Glucopyranoside with Photochemically Generated Hydroxyl Radicals, Journal of Wood Chemistry and Technology, 20(4), 375-394 (2000).
Guay et al., Mechanisms of Oxidative Degradation of Carbohydrates During Oxygen Delignification. II. Reaction of Photochemically Generated Hydroxyl Radicals with Methyl b-Cellobioside, Journal of Wood Chemistry and Technology, 21(1), 67-79 (2001).
Guay et al., Mechanisms of Oxidative Degradation of Carbohydrates During Oxygen Delignification. III. Reaction of Photochemically Generated Hydroxyl Radicals with 1,5-Anhydrocellobitol and Cellulose, 2002 TAPPI Fall Conference & Trade Fair.
Sihtola et al., Comparison and Conversion of Viscosity and DP-Values Determined by Different Methods, Paperi ja Puu 45:225 (1963).

* cited by examiner

*Primary Examiner* — Layla Bland
(74) *Attorney, Agent, or Firm* — Quarles & Brady LLP (57) ABSTRACT

Methods for depolymerizing polysaccharides are disclosed. In certain exemplary methods, polysaccharides having a first average molecular weight can be reacted with hydroxyl free radicals to produce polysaccharides having a second average molecular weight lower than the first average molecular weight. The hydroxyl free radicals can be formed by interaction of an oxidant with a catalyst comprising a polydentate ligand complexed with a metal ion. In certain exemplary embodiments, the oxidant can be hydrogen peroxide, and the catalyst can be iron methylglycine diacetate or iron-2,3,4,5,6 pentahydroxyhexanoate.

17 Claims, 3 Drawing Sheets

SYSTEMS, COMPOSITIONS, AND/OR METHODS FOR DEPOLYMERIZING CELLULOSE AND/OR STARCH

CROSS-REFERENCES TO RELATED APPLICATIONS

This application claims priority from U.S. Provisional Patent Application No. 60/916,376 filed May 7, 2007.

STATEMENT REGARDING FEDERALLY SPONSORED RESEARCH

Not Applicable.

BACKGROUND OF THE INVENTION

1. Field of the Invention

The invention relates to methods for depolymerizing polysaccharides in which polysaccharides are reacted with hydroxyl free radicals to produce polysaccharides having lower molecular weights. The hydroxyl free radicals are formed by interaction of an oxidant with a catalyst comprising a ligand complexed with a metal ion, such as iron methylglycine diacetate or iron-2,3,4,5,6 pentahydroxyhexanoate. The invention also relates to a method for producing glucose. The invention further relates to a method for producing ethanol.

2. Description of the Related Art

Due to rising oil prices, there has been ever increasing interest in the use of ethanol as fuel. Ethanol is typically produced by fermenting sugars using certain species of yeast. The sugars are often obtained by hydrolyzing starches to produce sugars such as glucose. This hydrolysis of starch into glucose can be accomplished by treatment with an acid and/or enzymes. Currently, the most common source for the starches used in ethanol production is corn. However, there has been concern that the diversion of corn from food uses to ethanol production may cause unwanted price increases in food products including corn.

As a result, there has been interest in using alternative crops, such as agricultural residues, wood, and various grasses, in ethanol production. In these crops, cellulose is the source of sugars for fermentation to ethanol. However, compared to corn starch ethanol production, several factors make cellulosic ethanol production more costly and less efficient. First, more effort is needed to pretreat and solubilize hemicellulose and cellulose because they are locked into a rigid cell wall structure with lignin. Harsher thermochemical pre-treatments may generate chemical by-products that inhibit enzyme hydrolysis and decrease the productivity of fermentative microbes. Second, the crystallinity of cellulose makes it more difficult for aqueous solutions of enzymes to convert cellulose to glucose.

Several processes have been proposed that could address the aforementioned disadvantages of cellulosic ethanol production. For example, processes have been developed that seek to improve the cellulase digestibility of cellulosic materials. U.S. Pat. No. 4,314,854 describes a process for enhancing the reactivity of cellulose-containing materials to cellulase enzymes by treating an aqueous suspension of the cellulose-containing material with hydrogen peroxide in the presence of a $Mn^{+2}$ ion forming manganese compound. U.S. Pat. Nos. 4,806,475 and 4,649,113 describe a process in which agricultural crop residues and other nonwoody lignocellulosic plant substrates are treated with $H_2O_2$ such that the substrates are partially delignified and the products of the treatment have low crystallinity and near quantitative cellulase digestibility.

It has also been reported that hydroxyl radicals react with cellulose by cleaving bonds between glucose units in the polymer chain (see Cole et al., "Mechanisms of Oxidative Degradation of Carbohydrates During Oxygen Delignification I. Reaction of Photochemically Generated Hydroxyl Radicals with Methyl-b-D-Glucoside," *Journal of Wood Chemistry and Technology*, 20:3, 2000; and Cole et al., "Mechanisms of Oxidative Degradation of Carbohydrates During Oxygen Delignification II. Reaction of Photochemically Generated Hydroxyl Radicals with Methyl-b-D-Cellobioside," *Journal of Wood Chemistry and Technology*, 21:1, 2001; and Guay et al., "Mechanisms of Oxidative Degradation of Carbohydrates During Oxygen Delignification III. Reaction of Photochemically Generated Hydroxyl Radicals with 1,5-Anhydrocellobiotol and Cellulose," *Journal of Pulp and Paper Science*, 28:7, 2002). Other uses of hydroxyl radicals and methods for generating hydroxyl radicals can be found in U.S. Pat. No. 6,960,330 to H. W. Cox, Jr.

However, there is still a need for alternative methods for depolymerizing cellulose or starch such that the cellulose or starch can be more easily hydrolyzed into sugars for fermentation into ethanol.

SUMMARY OF THE INVENTION

The foregoing needs are met by a method according to the invention for depolymerizing polysaccharides such as cellulose or starch. In the method, polysaccharides can be reacted with hydroxyl free radicals to produce polysaccharides having lower molecular weights. The hydroxyl free radicals can be formed by interaction of an oxidant with a catalyst comprising a ligand complexed with a metal ion, such as iron methylglycine diacetate or iron-2,3,4,5,6 pentahydroxyhexanoate.

In one aspect, the invention provides a method for depolymerizing polysaccharides such as cellulose and/or starch. In certain exemplary embodiments of the method, polysaccharides having a first average molecular weight can be reacted with hydroxyl free radicals to produce polysaccharides having a second average molecular weight lower than the first average molecular weight. The hydroxyl free radicals can be formed by interaction of an oxidant with a catalyst comprising a ligand complexed with a metal ion. The lower molecular weight polysaccharides, such as cellulose and/or starch, can be more easily hydrolyzed (e.g., by enzymatic hydrolysis) into sugars for fermentation into ethanol.

In certain exemplary embodiments, the oxidant can be hydrogen peroxide, and the catalyst can be iron methylglycine diacetate, which can be formed by mixing a source of iron ions (e.g., iron chloride) and a ligand source (methylglycine diacetic acid). In other exemplary embodiments, the oxidant can be hydrogen peroxide, and the catalyst can be iron-2,3,4,5,6 pentahydroxyhexanoate, which can be formed by mixing a source of iron ions (e.g., iron chloride) and a ligand source (e.g., gluconic acid).

In certain exemplary embodiments, the method can include (i) a Kraft pulping step to produce a pulp including cellulose, (ii) oxidant/catalyst treatment of the cellulose according to the invention, (iii) washing of the treated cellulose, (iv) enzymatic hydrolysis of the washed cellulose into sugars, and/or (v) fermentation of the resulting sugars into ethanol. The method can be seven times more energy efficient than corn starch ethanol production and can be 10% less expensive than corn starch ethanol production. The method need not require mechanical grinding (which can require over nine times more energy than Kraft pulping).

In certain exemplary embodiments, the method can include (i) a dry grinding step in which corn kernels are milled into meal, (ii) oxidant/catalyst treatment of the milled corn, optionally in the presence of alpha amylase, (iii) liquefaction of the treated milled corn, (iv) enzymatic hydrolysis of the corn into sugars such as by way of glucoamylase, and/or (v) fermentation of the resulting sugars into ethanol.

BRIEF DESCRIPTION OF THE DRAWINGS

A wide variety of embodiments will be more readily understood through the following detailed description of certain exemplary embodiments, with reference to the accompanying exemplary drawings in which.

DETAILED DESCRIPTION

Certain exemplary embodiments of the invention can provide a method of depolymerizing carbohydrates, such as cellulose and/or starch molecules, into low-molecular-weight polysaccharides using hydroxyl free radicals. Certain exemplary embodiments can provide a method of depolymerizing carbohydrates, such as cellulose and/or starch molecules, into low molecular weight polysaccharides using hydroxyl-free radicals wherein the free radicals can be produced from the interaction of an oxidant, such as hydrogen peroxide, and a catalyst comprising a ligand complexed with a metal ion, such as iron methylglycine diacetate (Fe-MGDA) or iron-2,3,4,5,6 pentahydroxyhexanoate.

One example embodiment of the invention provides a method for depolymerizing polysaccharides. In the method, polysaccharides having a first average molecular weight are reacted with hydroxyl free radicals to produce polysaccharides having a second average molecular weight lower than the first average molecular weight. The hydroxyl free radicals can be formed by interaction of an oxidant with a catalyst comprising a ligand complexed with a metal ion. The second average molecular weight can be at least 50% lower than the first average molecular weight. Preferably, the second average molecular weight is at least 75% lower than the first average molecular weight. More preferably, the second average molecular weight is at least 85% lower than the first average molecular weight. The oxidant can be added at about 1% to about 10% by weight of the polysaccharides. The catalyst can be added at an oxidant to catalyst weight ratio of about 1:3 to about 9:1.

The polysaccharides having a first average molecular weight can be reacted with the hydroxyl free radicals at an adjusted pH in the range of 5.0 to 10.0. Preferably, the polysaccharides having a first average molecular weight are reacted with the hydroxyl free radicals at a pH in the range of 6.0 to 9.0. More preferably, the polysaccharides having a first average molecular weight are reacted with the hydroxyl free radicals at a pH in the range of 7.0 to 9.0. Optionally, the pH can be adjusted above 10.0 after the pH is adjusted to 5.0 to 10.0, or 6.0 to 9.0, or 7.0-9.0. In one version of the invention, the polysaccharides are reacted at a pressure above atmospheric pressure.

Another example embodiment of the invention provides a method for producing ethanol. In the method, polysaccharides having a first average molecular weight are reacted with hydroxyl free radicals to produce polysaccharides having a second average molecular weight lower than the first average molecular weight. The hydroxyl free radicals can be formed by interaction of an oxidant with a catalyst comprising a ligand complexed with a metal ion. The polysaccharides having the second average molecular weight are hydrolyzed into at least one sugar, and the sugar is fermented into ethanol typically using an enzyme. The polysaccharides having the second average molecular weight can be washed before hydrolyzing.

In this embodiment of the invention, the second average molecular weight can be at least 50% lower than the first average molecular weight. Preferably, the second average molecular weight is at least 75% lower than the first average molecular weight. More preferably, the second average molecular weight is at least 85% lower than the first average molecular weight. The oxidant can be added at about 1% to about 10% by weight of the polysaccharides. The catalyst can be added at an oxidant to catalyst weight ratio of about 1:3 to about 9:1.

The polysaccharides having a first average molecular weight can be reacted with the hydroxyl free radicals at an adjusted pH in the range of 5.0 to 10.0. Preferably, the polysaccharides having a first average molecular weight are reacted with the hydroxyl free radicals at a pH in the range of 6.0 to 9.0. More preferably, the polysaccharides having a first average molecular weight are reacted with the hydroxyl free radicals at a pH in the range of 7.0 to 9.0. Optionally, the pH can be adjusted above 10.0 after the pH is adjusted to 5.0 to 10.0, or 6.0 to 9.0, or 7.0-9.0. In one version of the invention, the polysaccharides are reacted at a pressure above atmospheric pressure.

Still another example embodiment of the invention provides a method for producing glucose. In this method, a material including starch or cellulose is contacted with hydroxyl free radicals formed by interaction of an oxidant with a catalyst comprising a ligand complexed with a metal ion, and the material is hydrolyzed (typically enzymatically) to produce glucose. The material can be washed before hydrolyzing. The material can be reacted with the hydroxyl free radicals at an adjusted pH in the range of 5.0 to 10.0. Preferably, the material is reacted with the hydroxyl free radicals at a pH in the range of 6.0 to 9.0. More preferably, the material is reacted with the hydroxyl free radicals at a pH in the range of 7.0 to 9.0. Optionally, the pH can be adjusted above 10.0 after the pH is adjusted to 5.0 to 10.0, or 6.0 to 9.0, or 7.0-9.0. In one version of the invention, the material is reacted at a pressure above atmospheric pressure.

Non-limiting examples of oxidants potentially suitable for use in certain exemplary embodiments can include: peroxides (e.g., hydrogen peroxide), ozone, hypochlorites (e.g., sodium hypochlorite), persulfates, permanganates, peracetic acid (PAA), chlorine dioxide, chlorites, halogens, and/or mixtures thereof.

The catalyst can be formed by mixing a ligand source (which provides the ligand) with a solution of a metal ion. An example method for forming the catalyst can comprise: (1) dissolving a greater than 0.1 M ligand source in water; (2) if the pH of the ligand source solution is 7 or less, adjusting the pH to 10-12, preferably 11-12, using a pH adjusting agent, such as sodium hydroxide and/or an equivalent; and/or (3) using an acidic solution of a metal, titrating to a pH of near neutral (5-9, preferably 6-8) to occupy most and/or all chelation sites of the ligand with the metal. The metal ion can be a transition metal ion such as an iron ion (e.g., ferrous ion or ferric ion) or a manganese ion. The ligand can be a polydentate ligand.

Non-limiting examples of ligand sources potentially suitable for use in certain exemplary embodiments can include: aminocarboxylic acids, heterocyclic carboxylic acids, polyhydroxy aromatics, polycarboxylic acids, monocarboxylic acids, macrocyclic tetraamido compounds, phosphonic acids, rhodizonic acid, tetrahydroxy-1,4-quinone, hexaketocyclohexane, and/or mixtures thereof.

Suitable aminocarboxylic acids can include, without limitation, ethylenediaminetetraacetic acid (EDTA); hydroxyethyleneiminodiacetic acid (HEIDA); nitrilotriacetic acid (NTA); N-(2-Hydroxyethyl)ethylenediamine-N,N',N'-triacetic acid (HEDTA); Ethylene glycol-bis(2-aminoethylether)-N,N,N',N'-tetraacetic acid (EGTA); methylglycinediacetic acid (MGDA); glutamic acid diacetic acid (GLDA); imidodiacetic acid; ethylenediaminetriacetic acid; and/or diethylenetriaminepentaacetic acid.

Suitable heterocyclic carboxylic acids can include, without limitation, picolinic acid (pyridine-2-carboxylic acid).

Suitable polyhydroxy aromatics can include, without limitation, gallic acid (3,4,5-trihydroxybenzoic acid); alizarin red (1,2-dihydroxyanthraquinone); rutin (2-(3,4-dihydroxyphenyl)-4,5-dihydroxy-3-[3,4,5-trihydroxy-6-[(3,4,5-trihydroxy-6-methyl-oxan-2-yl)oxymethyl]oxan-2-yl]oxy-chromen-7-one); catechin (2-(3,4-dihydroxy-phenyl) chroman-3,5,7-triol)); and/or pyrocatechol (1,2-dihydroxybenzene)

Suitable polycarboxylic acids and monocarboxylic acids can include, without limitation, gluconic acid (2,3,4,5,6-pentahydroxycaproic acid); citric acid (2-hydroxy-1,2,3-propanetricarboxylic acid); malonic acid (propanedioic acid); oxalic acid (ethanedioic acid); ascorbic acid ((R)-3,4-dihydroxy-5-((S)-1,2-dihydroxyethyl)furan-2(5H)-one); and/or tartaric acid (2,3-dihydroxybutanedioic acid).

Suitable phosphonic acids can include, without limitation, amino tri methylene phosphonic acid; hydroxyethylidene 1,1-diphosphonic acid; hexamethylene diamine tetra methylene phosphonic acid; diethylene triamine penta methylene phosphonic acid; bis hexamethylene triamine penta methylene phosphonic acid; and/or phosphonobutane tricarboxylic acid.

Certain exemplary embodiments can be combined with alternative methods of depolymerizing cellulose and/or starch molecules such as: (i) acid hydrolysis using dilute mineral acids such as sulfuric acid, (ii) acid hydrolysis using concentrated mineral acids, and/or (iii) enzymatic hydrolysis.

When cellulosic materials are used in certain exemplary embodiments, the cellulose can come from a Kraft, sulfite, and/or soda pulping process and/or can include mainly cellulose and/or some lignin. The concentration of cellulose and/or lignin can vary according to the pulping process. The majority of the lignin and/or the hemicellulose might have been removed during the pulping process. Another pulp/carbohydrate source is solvent treated pulp known as organosolv pulp which refers to various pulps treated with solvent to remove undesirable portions of the pulp such as lignin or hemicellulose. The cellulose can come from hardwood and/or softwood trees, grasses such as switchgrass and miscanthus grass, and/or from other cellulose plants and/or other plant residues such as corn stover. Other sources of cellulose can include, without limitation, sugar beet pulp, sugar cane stalks, and/or bagasse. When starch is used in certain exemplary embodiments, the starch can come from corn and/or other crops such as potatoes, rice and wheat. In one form, the starch can be contained in milled corn produced by a dry grind process.

Some variables that can control the free radical depolymerization in certain exemplary embodiments can be: (i) time of reaction, (ii) temperature, (iii) concentration of oxidant, (iv) concentration of the catalyst, (v) pH of the mixture, (vi) type of oxidant, and/or (vii) type of catalyst. For example. the selected masses of oxidants and catalyst within a treatment can control mass of hydroxyl radicals produced. Also, the flow rate, residence time, etc., can be adjusted to conduct treatment using a continuous flow system design.

EXAMPLES

The following examples can serve to further illustrate certain exemplary embodiments.

In the examples, the method of measuring the depolymerization of the cellulose is "pulp viscosity" which can correlate to the degree of polymerization which can correlate to molecular weight.

Preparing a First Example Catalyst

One method of preparing a Fe-MGDA catalyst is to directly mix with methylglycinediacetic acid (MGDA) and a source of iron ions (e.g., ferrous ions or ferric ions), such as an aqueous solution of an iron salt, such as iron perchlorate, iron nitrate, iron citrate, iron malate, iron lactate, and/or iron oxalate, etc. Another method is to mix a liquid iron (III) chloride solution with MGDA. Iron (III) chloride can be purchased as a ~13% iron solution with a pH of about 1.0 to about 1.5 from Univar, Martinsville, Va., USA, in 55 gallon drum and tanker load quantities.

The chelating agent MGDA, which is sometimes referred to as methylglycinediacetate and/or as trisodium methylglycinediacetate, can be purchased from BASF Corp., Mount Olive, N.J., USA, under their product name, Trilon® M. It can be purchased as a 39% concentrated liquid in 55 gallon drum and tanker load quantities. Trilon® M has a density of 1.29-1.33 g/cm$^3$, a pH of about 10.0 to about 12.0 (1% in water, 23° C.), and a molecular weight of MGDA-Na$_3$: 271 g/mol.

Formulation of one liter of the iron chelate Fe-MGDA (referred to in Table 6 below as VTX) can be made by adding 52.3 milliliters (~27 grams of MGDA-Na$_3$ depending on density) of Trilon® M liquid to approximately 800 milliliters of water. This solution can be then mixed continuously with a magnetic stir bar or other mechanical mixing technique. Liquid iron chloride solution can be added to the solution while the pH of the mixture is monitored. The pH of Trilon® M/water mixture can be from 10 to 12 initially. Iron chloride can be added until the pH of the solution comes down to a pH of about 7.0. Water can be added to achieve a final volume of 1000 millimeters. At this point, the Fe-MGDA can be ready for use. Larger volumes can be produced by scaling-up this formulation. In various alternative embodiments, liquid iron chloride solution can be added to undiluted MGDA.

Preparing a Second Example Catalyst

A 1.0 M catalyst (referred to in Table 6 below as VTH) can be prepared as follows: (1) Add 218 grams (1.0 M) of technical grade sodium gluconate (2,3,4,5,6-pentahydroxycaproic acid sodium salt) to 700 milliliters of de-chlorinated tap water or equivalent. Mix solution to completely dissolve the sodium gluconate. (2) Add 59 milliliters of 50% sodium hydroxide to the mixture and continue to mix. (3) Slowly add 113 milliliters of 38-40% iron chloride solution to the solution while monitoring pH with continued mixing to form iron-2,3,4,5,6 pentahydroxyhexanoate. The pH of the final solution should be circum-neutral (6.5-7.5). Adjustments back into the circum-neutral range can be made with caustic soda (if below 6.5) or with ferric chloride (if above 7.5).

Example 1

Northern unbleached softwood Kraft pulp was treated according to Trial 1 Plan in Table 1 below using hydrogen peroxide (HOOH) and iron methylglycine diacetate (Fe-MGDA) as the catalyst.

TABLE 1

Trial 1 Plan

| Atmospheric Hydrogen Peroxide Bleaching | | Pressurized Hydrogen Peroxide Bleaching | |
|---|---|---|---|
| HOOH Charge (% based on Oven Dry Pulp) | 2.5% & 5.0% | HOOH Charge (% based on Oven Dry Pulp) | 2.5% |
| NaOH Charge (% based on Oven Dry Pulp) | Adjust pH to 8.5 | NaOH Charge (% based on Oven Dry Pulp) | Adjust pH to 8.5 |
| Pulp Consistency | 15.0% | Pulp Consistency | 15.0% |
| Temperature | 60° C. | Temperature | 90° C. |
| Retention Time | 45 min. | Retention Time | 30 min. |
| Catalyst Ratio (HOOH:Catalyst) | No Catalyst, 1:1, 3:1, 6:1, 9:1 | Catalyst Ratio (HOOH:Catalyst) | No Catalyst, 1:1, 3:1, 6:1, 9:1 |
| | | Oxygen Pressure | 100 psig |

Yield, kappa number and viscosity were determined for each pulp sample after bleaching. Kappa number measurements determined the lignin removal efficiency and viscosity measurements identified changes to the cellulose degree of polymerization.

Table 2 summarizes the results for the atmospheric hydrogen peroxide bleaching trials of Table 1. Pulp yields were statistically the same for the control and catalyst experiments. Pulp degree of polymerization values are also included in Table 2 which are based on published values of pulp viscosity (see, Sihtola et al., "Comparison and Conversion of Viscosity and DP-Values Determined By Different Methods," *Paperi ja Puu* 45:225, 1963). Pulp yields for bleaching are typically 99% which indicates that the catalyst had no affect on pulp yield. Pulp viscosity is a measure of the cellulose degree of polymerization. The pulp viscosity dropped linearly as the catalyst addition rate increased. Viscosity response to catalyst addition during the atmospheric hydrogen peroxide experiments is plotted in FIG. 1. Linear regression analysis of the slope gave an $R^2$ value of 0.9522 indicating strong statistical evidence that the pulp viscosity drop correlated linearly with the catalyst addition rate.

TABLE 2

Atmospheric Hydrogen Peroxide Bleaching Results Summary

| IPS Experiment # | Catalyst Ratio (HOOH: Catalyst) | Pulp Yield (%) | Pulp Viscosity (cp) | Pulp Degree of Poly- merization | Kappa Number |
|---|---|---|---|---|---|
| Control | Control | | 51.6 | 2000 | 24.1 |
| 1 | None | 99.8 | 48.9 | 1950 | 23.6 |
| 2 | None | 99.4 | 49.7 | 1980 | 23.4 |

TABLE 2-continued

Atmospheric Hydrogen Peroxide Bleaching Results Summary

| IPS Experiment # | Catalyst Ratio (HOOH: Catalyst) | Pulp Yield (%) | Pulp Viscosity (cp) | Pulp Degree of Poly- merization | Kappa Number |
|---|---|---|---|---|---|
| 3 | None | 98.6 | 50.2 | 1980 | 23.4 |
| 4 | 1:1 | 98.2 | 9.8 | 880 | 23.0 |
| 5 | 1:1 | 98.6 | 10.8 | 900 | 22.9 |
| 6 | 1:1 | 98.4 | 10.9 | 900 | 23.0 |
| 7 | 3:1 | 99.8 | 25.5 | 1510 | 24.2 |
| 8 | 3:1 | 98.5 | 20.7 | 1390 | 24.2 |
| 9 | 3:1 | 99.1 | 22.6 | 1420 | 24.3 |
| 10 | 6:1 | 98.7 | 35.2 | 1750 | 24.1 |
| 11 | 6:1 | 99.7 | 34.8 | 1750 | 24.3 |
| 12 | 6:1 | 98.7 | 35.5 | 1760 | 24.1 |
| 13 | 9:1 | 98.7 | 41.8 | 1830 | 24.3 |
| 14 | 9:1 | 99.1 | 40.6 | 1820 | 24.3 |
| 15 | 9:1 | 99.7 | 44.4 | 1850 | 24.6 |

Since pulp viscosity can be a measure of the cellulose degree of polymerization, the atmospheric hydrogen peroxide experiments were viewed as successful at breaking down the cellulose. The average degree of polymerization decreased from 2000 for the untreated pulp to 900 for the pulp treated with the 1:1 peroxide to catalyst ratio. The cleavage of the cellulose chains increased as the catalyst dosage increased.

The atmospheric peroxide treatments were successful at removing lignin from the pulp. A potential ultimate goal for the bleaching of pulp is to remove all of the lignin (Kappa number ~0-1) while protecting cellulose (in this case, maintain a Kappa number of 51.6). The only experiment that was statistically different than the others was the 1:1 catalyst to peroxide ratio. In this experiment 4.5% of the lignin was removed, but the cellulose viscosity was lowered 80%.

Without intending to be bound by theory, it is believed that hydroxyl radicals can be used to activate lignin for bleaching by modifying sites in the lignin polymer. Because hydroxyl radicals can react with lignin and/or cellulose, the correct dosage that will activate the lignin without severely degrading cellulose can be used. The 9:1 and 6:1 hydrogen peroxide to catalyst ratios might be most preferable. After activating the lignin, the pulp can be brought back to a high pH to facilitate reactions with hydrogen peroxide and/or lignin under typical bleaching conditions. We currently envision a pretreatment of the pulp with the catalyst and/or hydrogen peroxide at a neutral pH, potentially followed by hydrogen peroxide bleaching at a pH of 11-12.

Table 3 summarizes the results for the pressurized hydrogen peroxide bleaching trials. Pulp yields were statistically the same for the control and catalyst experiments. Pulp degree of polymerization values are also included in Table 3 which are based on published values of pulp viscosity (see Sihtola, et al., supra). Pulp yields for bleaching are typically 99% which indicates that the catalyst had no affect on pulp yield.

TABLE 3

Pressurized Hydrogen Peroxide Bleaching Results Summary

| IPS Experiment # | Catalyst Ratio (HOOH: Catalyst) | Pulp Yield (%) | Pulp Viscosity (cp) | Pulp Degree of Poly- merization | Kappa Number |
|---|---|---|---|---|---|
| Control | Control | | 51.6 | 2000 | 24.1 |
| 16 | None | 99.1 | 36.1 | 1760 | 21.3 |
| 17 | None | 99.3 | 34.6 | 1750 | 22.1 |
| 18 | None | 99.8 | 35.2 | 1750 | 22.6 |
| 19 | 1:1 | 98.4 | 7.0 | 670 | 20.7 |

TABLE 3-continued

Pressurized Hydrogen Peroxide Bleaching Results Summary

| IPS Experiment # | Catalyst Ratio (HOOH:Catalyst) | Pulp Yield (%) | Pulp Viscosity (cp) | Pulp Degree of Polymerization | Kappa Number |
|---|---|---|---|---|---|
| 20 | 1:1 | 99.3 | 7.3 | 680 | 20.6 |
| 21 | 1:1 | 97.6 | 7.8 | 690 | 21.2 |
| 22 | 3:1 | 98.3 | 15.7 | 1200 | 20.9 |
| 23 | 3:1 | 98.8 | 16.4 | 1220 | 21.0 |
| 24 | 3:1 | 98.4 | 9.5 | 840 | 20.2 |
| 25 | 6:1 | 99.0 | 10.5 | 900 | 20.1 |
| 26 | 6:1 | 99.3 | 22.3 | 1420 | 21.5 |
| 27 | 6:1 | 100.0 | 21.7 | 1410 | 21.5 |
| 28 | 9:1 | 99.3 | 17.6 | 1280 | 21.0 |
| 29 | 9:1 | 99.1 | 11.5 | 1000 | 20.1 |
| 30 | 9:1 | 99.1 | 25.6 | 1510 | 21.6 |

Figure 2:
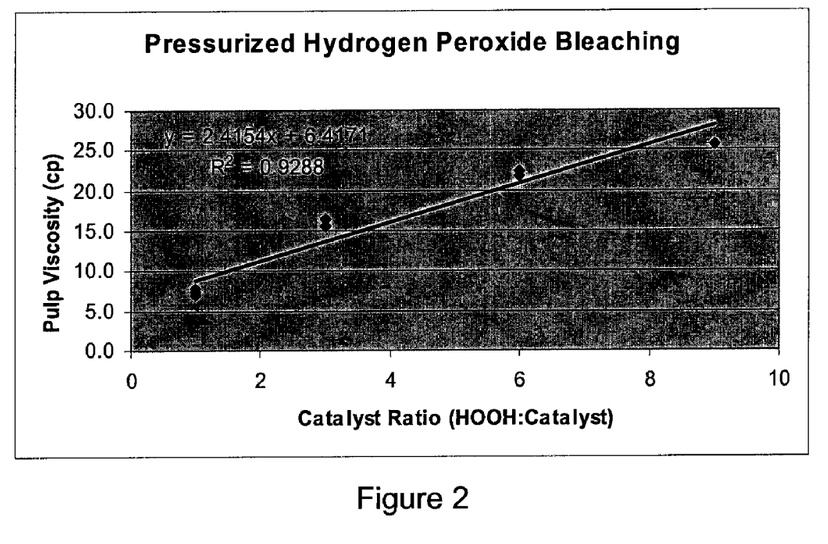
FIG. 2 shows a plot of pulp viscosity vs. hydrogen peroxide to catalyst (Fe-MGDA) ratio for the "Pressurized Hydrogen Peroxide Bleaching" test of Example 1.

The pulp viscosity dropped as the catalyst addition rate increased. The drop was not as linear as the drop measured in the atmospheric bleaching experiments. Viscosity response to catalyst addition during the atmospheric hydrogen peroxide experiments is plotted in FIG. 2. The $R^2$ value in FIG. 2 is 0.9288 which indicated that the response of viscosity to catalyst dosage could be linear as it was in the atmospheric experiments.

Pulp viscosity might drop during normal oxygen bleaching conditions due to the formation of a small amount of hydroxyl radicals that can form as byproducts from reactions with oxygen and/or lignin. The combination of oxygen, hydrogen peroxide, and/or catalyst appeared able to lower the cellulose degree of polymerization more than the hydrogen peroxide and catalyst alone. The 1:1 catalyst to peroxide ratio appeared able to lower the cellulose degree of polymerization from 2000 to 680, which is more than 200 units lower than the atmospheric bleaching conditions with the same catalyst dosage. As the catalyst dosage increased, the cellulose degree of polymerization decreased.

The pressurized peroxide treatments were successful at removing lignin from the pulp. Samples number 18 and 26 were selected to perform an alkaline extraction on these pulps. If the bleaching conditions had degraded lignin, an alkaline extraction would make the lignin fragments soluble in the liquor for removal. The experimental results of the two extraction experiments indicated that the Kappa number of the pulps after alkaline extraction were lowered by approximately 1 Kappa unit each. These results indicate that the lignin was not degraded extensively enough during bleaching to be removed by alkaline extraction.

Figure 1:
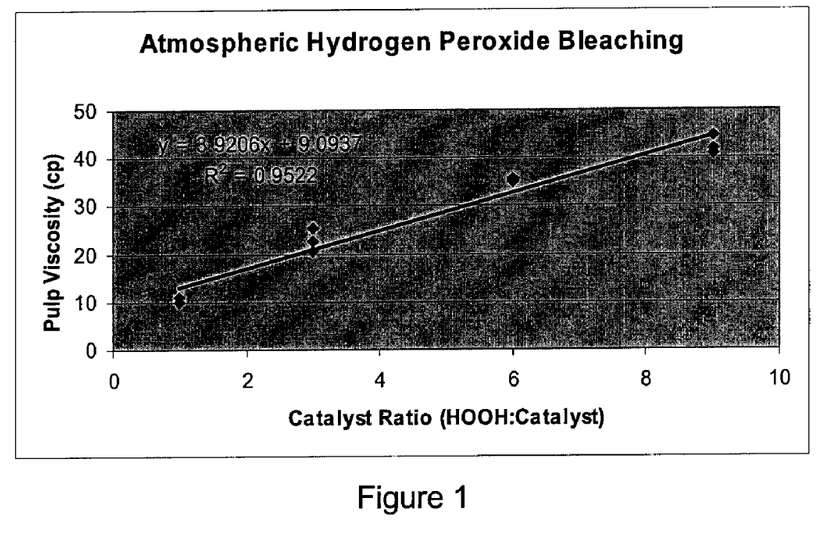
FIG. 1 shows a plot of pulp viscosity vs. hydrogen peroxide to catalyst (Fe-MGDA) ratio for the "Atmospheric Hydrogen Peroxide Bleaching" test of Example 1.

Thus, Example 1 shows that the iron methylglycine diacetate catalyst in combination with hydrogen peroxide was very successful at breaking down the cellulose into a shorter chain polymer. FIGS. 1 and 2 show that the degradation of cellulose is dependent on the catalyst dosage and the response appears to be linear.

Example 2

Northern unbleached softwood Kraft pulp was treated according to Trial 2 Plan in Table 4 below using hydrogen peroxide (HOOH) and iron methylglycine diacetate (Fe-MGDA) as the catalyst.

TABLE 4

Trial 2 Plan
Atmospheric Hydrogen Peroxide Bleaching

| | |
|---|---|
| HOOH Charge (5 based on Oven Dry Pulp) | 2.5% & 5.0% |
| NaOH Charge (% based on Oven Dry Pulp) | Adjust pH to 8.5 |
| Pulp Consistency | 15.0% |
| Temperature | 60° C. |
| Retention Time | 45 min. |
| Catalyst Ratio (HOOH:Catalyst) | 1:1 & 1:2 |

Table 5 summarizes the results for the atmospheric hydrogen peroxide bleaching trials of Table 4.

TABLE 5

TRIAL 2 RESULTS

| Experiment | % HOOH (Based on OD Pulp) | Retention Time (min) | Catalyst Ratio (HOOH:Catalyst) | Pulp Viscosity (cp) | Pulp Degree of Polymerization | End pH | Kappa Number |
|---|---|---|---|---|---|---|---|
| Control | | | | 50.02 | 2000 | | 23.89 |
| 31 | 2.5 | 45 | 1:1 | 15.33 | 1220 | 5.73 | 23.05 |
| 32 | 2.5 | 1000 | 1:1 | 5.63 | 550 | 3.95 | 21.96 |
| 33 | 2.5 | 45 | 1:1 | 7.25 | 680 | 4.73 | 21.80 |
| 34 | 2.5 | 45 | 1:2 | 19.27 | 1340 | 5.91 | 22.51 |
| 35 | 2.5 | 45 | 1:2 | 23.85 | 1470 | 5.91 | 23.18 |
| 36 | 2.5 | 45 | 1:2 | 19.93 | 1360 | 6.01 | 23.27 |
| 37 | 2.5 | 1000 | 1:2 | 4.93 | ~450 | 5.02 | 20.33 |
| 38 | 2.5 | 45 | 1:2 | 12.02 | 1020 | 5.59 | 22.82 |
| 39 | 5.0 | 45 | 1:1 | 19.89 | 1360 | 5.78 | 23.30 |
| 40 | 5.0 | 45 | 1:1 | 6.41 | 600 | 4.74 | 22.80 |
| 41 | 5.0 | 45 | 1:1 | 14.10 | 1160 | 5.51 | 23.25 |
| 42 | 5.0 | 1000 | 1:1 | 11.00 | 950 | 3.87 | 22.54 |
| 43 | 5.0 | 45 | 1:1 | 13.78 | 1110 | 5.67 | 23.20 |
| 44 | 5.0 | 45 | 1:2 | 12.47 | 1050 | 5.74 | 22.80 |
| 45 | 5.0 | 45 | 1:2 | 10.62 | 920 | 5.45 | 22.70 |
| 46 | 5.0 | 45 | 1:2 | 11.43 | 980 | 6.02 | 24.30 |

Experiments 31, 34, 35, 36, 39, 40, 41, 44, 45, 46 - Catalyst was added to the pulp before the hydrogen peroxide.
Experiments 32, 33, 37, 42, 43 - The catalyst was diluted and added with the hydrogen peroxide at the same time.
Kappa Number measures lignin content.
[Note:
A system that maintains the pH of the treatment at ~7.0 throughout a treatment cycle will result in more hydroxyl radical formation per unit of peroxide added.]

In Trial 2 of Table 4, larger viscosity drops were observed than Trial 1 of Table 1 for several experiments. The lowest degree of polymerization observed was ~450.

Thus, certain exemplary embodiments can provide a method for depolymerizing polysaccharides. Certain exemplary embodiments can reduce pulp viscosity from about 50 centipoise to less than 5 centipoise. This represents a deduction of the degree of polymerization from 2000 to less than 450.

Example 3

Experiments were undertaken to measure the glucose yield from cellulose and starch after treatment with hydroxyl radicals. The source of cellulose for the experiments was commercially available softwood Kraft pulp, hardwood Kraft pulp, and manufactured pulp from miscanthus grass and corn stover. Ground corn was the starch source.

Experiments sought to determine experimental conditions to reduce the cellulose degree of polymerization in pulp. Reducing the cellulose degree of polymerization would make the cellulose polymer more accessible to enzymes to produce glucose. Cellulose degree of polymerization was estimated by measuring the pulp viscosity following TAPPI test method T 230 (See Sihtola, supra). Table 6 below lists the experimental results for each pulp type in regards to cellulose depolymerization. Experimental conditions for initial temperature and pulp consistency were held constant for all experiments at 90° F. and 20% consistency. All reactions were conducted using a Mark V Laboratory Mixer/Reactor manufactured by Quantum Technologies with intermittent mixing at 15 hertz for 2 seconds every 20 seconds for a total reaction time of 2 hours. Hydrogen peroxide was dosed in 5 equal doses at five minute intervals. The preparation of the VTX and VTH catalyst is described above.

cellulose sample, suspend in 100 milliliters of reaction solution (90 milliliters 0.5 M Citrate buffer, pH 4.8, 10 milliliters Genencor® GC220 cellulase enzyme mixture), react for 24 hours, shaking, at 50° C., remove 1 milliliter sample for sugar analysis. Sugar yield was estimated using a modified dinitro salicylic acid (DNS) method for determining reducing sugars. This method measures all sugars with a reducible aldehyde end group. These measurements showed an increase in the rate and total amount of sugars produced from all four pulps after treatment with the catalyst system at the dosages listed in Table 6. After reviewing the data, a recommended dosage of 1 or 2 milliliters of enzyme was considered a viable commercial dosage. In addition, the yield of the specific sugar glucose is what determines the potential ethanol yield. To reinforce the earlier data, enzyme treated pulp samples were obtained for HPLC analysis to measure glucose content.

Samples of saccharified unbleached softwood Kraft pulp and miscanthus grass pulp were analyzed using a Waters HPLC. Each condition represents an enzyme treatment of 5 oven dry grams of pulp with 2 milliliters of a Genencor® GC220 enzyme mixture. The enzyme treatments were carried out and frozen before HPLC. The pulp treatment conditions and glucose yields are included in FIG. 3. Both treated pulp samples are identical, but one sample was washed with water to remove the catalyst system chemicals and the other was taken directly from the Quantum mixer.

Figure 3:
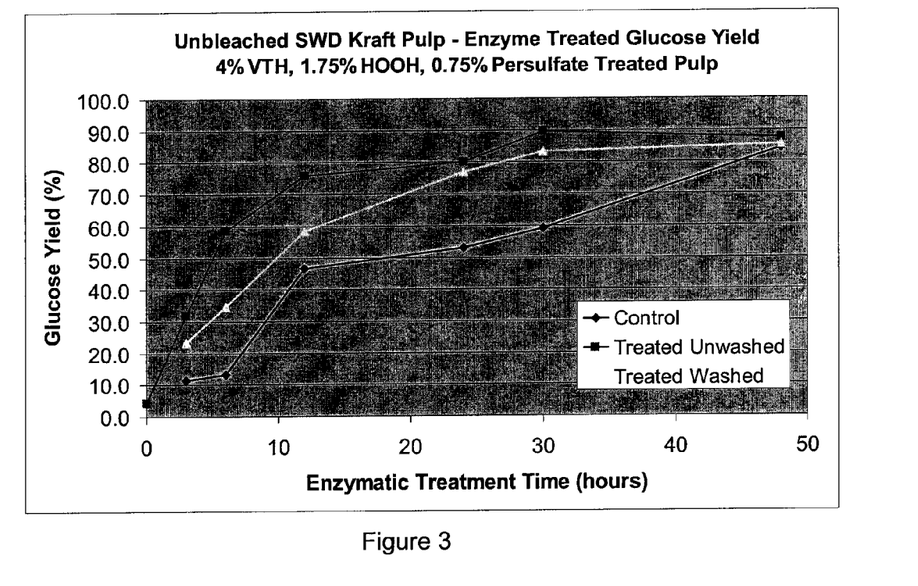
FIG. 3 shows a plot of glucose yield vs. enzymatic treatment time for unbleached softwood kraft pulp after treatment with hydroxyl radicals.

Glucose yields in FIG. 3 are based on the actual glucose content in the starting material which was measured. The catalyst system treatment of the softwood Kraft pulp dramatically increased the rate of glucose production. Maximum glucose yield was obtained between 24-30 hours in the treated samples versus 30-48 hours in the control. The final yield of glucose was the same in the treated versus the control sample which indicates that the catalyst system will not lower the

TABLE 6

Pulp Cellulose Depolymerization

| Sample | Catalyst & Dosage | Oxidant & Dosage | Initial pH | Final pH | Initial Viscosity (cp) | Final Viscosity (cp) | Initial Cellulose DP | Final Cellulose DP |
|---|---|---|---|---|---|---|---|---|
| Unbleached Softwood Kraft | VTH 2.5% | HOOH 2.5% | ~7 | ~3 | 50 | 3.8 | 2000 | 300 |
| Unbleached Hardwood Kraft | VTX 5.6% | HOOH 3.5% | ~7 | ~4 | 20 | 3.8 | 1350 | 300 |
| Unbleached Miscanthus Pulp | VTX 5.6% | HOOH 3.5% | ~7 | ~6 | 5 | 5 | 470 | 470 |
| Unbleached Corn Stover Pulp | VTX 5.6% | HOOH 3.5% | ~7 | ~6 | 5.8 | 3.8 | 540 | 300 |

The results above show that the catalyst treatment forms hydroxyl radicals which depolymerize cellulose. Hydroxyl radicals reduce the cellulose degree of polymerization more dramatically in samples with longer initial cellulose chains. After proving the catalyst treatments were capable of depolymerizing cellulose, we sought to measure an increase in the rate and yield of glucose production through enzymatic saccharification. In the softwood, an 85% decrease of the degree of polymerization from 2000 to 300 occurred.

Experiments showed that treatments of all four pulps increased the yield of reducing sugars through enzymatic saccharification. Enzymatic saccharification conditions for each pulp sample were as follows: Weigh out 5000 milligrams overall glucose yield. The HPLC results also mirror the reducing sugar analysis on the same pulp which supports the earlier sugar yield results obtained. The glucose yields above also indicate that the catalyst system will not inhibit the saccharification enzymes provided the reaction is complete.

Miscanthus grass pulp samples were also analyzed. The treatment conditions and glucose yields are included in FIG. 4. Each condition represents an enzyme treatment of 5 oven dry grams of pulp with 2 ml of a Genencor® GC220 enzyme mixture.

Figure 4:
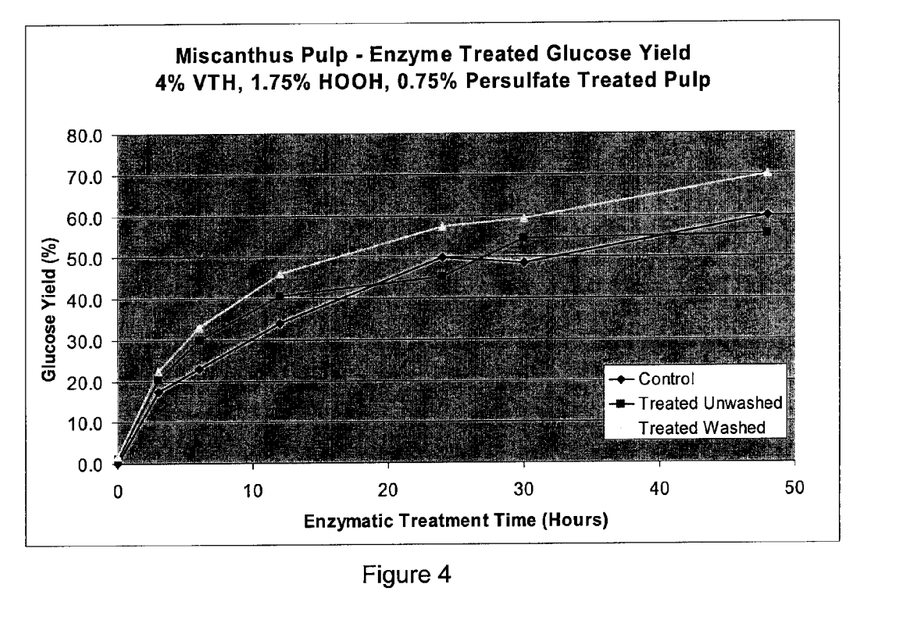
FIG. 4 shows a plot of glucose yield vs. enzymatic treatment time for miscanthus pulp after treatment with hydroxyl radicals.

Glucose yields in FIG. 4 are based on the oven dry weight of the total pulp. The glucose yield increase measured above mirrors earlier results measured with the miscanthus grass pulp using the reducing sugar method. Glucose formation rate increases but to a lesser extent than the softwood pulp. Miscanthus grass pulp contains shorter cellulose chains than softwood pulp so the initial enzyme activity is higher on the control pulp. However, the catalyst treatment still increases the rate of glucose formation through enzymatic saccharification.

Glucose yield measurements confirmed the experimental results that the catalyst system treatment of all four pulp types increases the rate of glucose formation using enzymes. The mechanism for the increase is that hydroxyl radicals cleave bonds between glucose molecules in the cellulose chain which provides more access locations for enzyme activity. The catalyst appears to have a greater effect on materials with longer chain cellulose polymers.

Enzyme saccharifications were carried out on treated corn starch samples to measure glucose yield. Starch pretreatments were done to ensure no losses due to freezing or spoilage. The autoclave step was skipped because antibiotics were added to each sample. Antibiotics were added (tetracycline at 0.4 ml/1 g dry weight of substrate and cycloheximide at 0.3 ml/1 g dry weight of substrate) to limit contamination. Saccharification enzymes used were liquozyme and spirizyme (2 microliters to each sample). Glucose yields based on the oven dry weight of corn assuming a 70% starch content are shown in FIG. 5 wherein the VTX and VTH catalyst are as described above.

Figure 5:
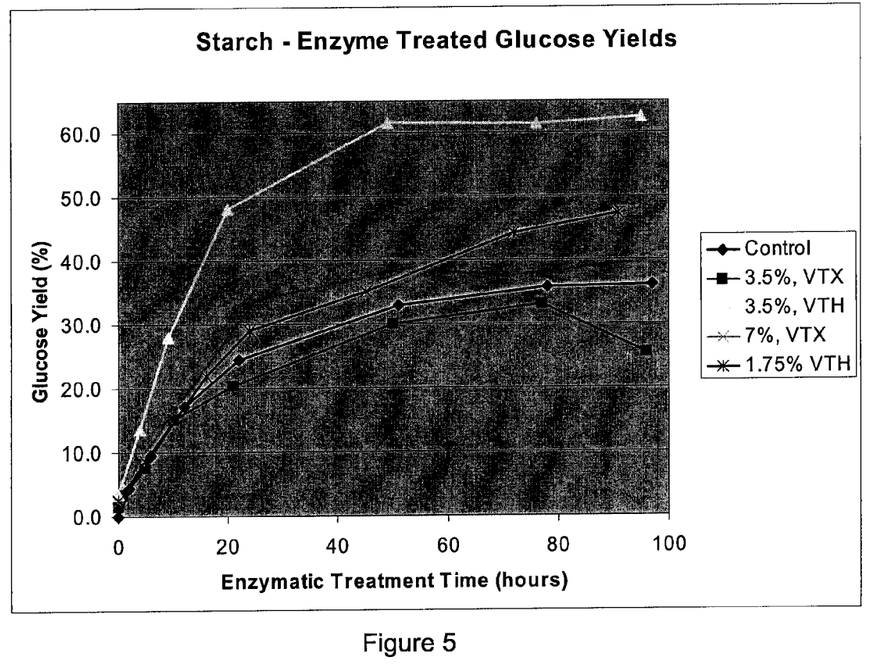
FIG. 5 shows a plot of glucose yield vs. enzymatic treatment time for corn starch after treatment with hydroxyl radicals.

The glucose yields in FIG. 5 were favorable. One of the largest operational bottlenecks in corn ethanol plants is due to the required gelatinization step in which corn starch is heated at 185° F. for two hours. Gelatinization opens up the starch molecules making them more accessible to the enzymes. A gelatinization step was not performed in the treatments. All samples were treated with both alpha amylase and glucoamylase as they would be in corn ethanol plants. The lack of gelatinization is clearly the cause of the low glucose yield for the control sample. The VTH treated corn samples achieved a higher glucose yield at a faster rate than the control. Certain VTX treated corn samples also achieved a higher glucose yield at a faster rate than the control. These results clearly show that the VTH and VTX catalyst system is depolymerizing the corn starch making it more available to the enzymes.

In certain exemplary embodiments, one or more transition metal (such as iron, copper, and manganese) chelate complexes can produce hydroxyl and/or free radicals at circumneutral pH conditions in combination with a variety of oxidants, including, for example, hydrogen peroxide, ozone, hypochlorite, peracetic acid, persulfate, permanganate, chlorine dioxide, and/or chlorite. Because hydroxyl and/or free radicals can be potent oxidizers, the transition metal chelate complexes in combination with the selected oxidants and/or combination of oxidants can successfully break bonds within starch and/or cellulose. It can be possible to stop the process at desirable end points for the purpose of producing ethanol by preparing starch, cellulose, and/or starch/cellulose combinations for fermentation to alcohols (such as ethanol and/or methanol).

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, abstract, drawing figure, attachment, etc.) of this application, unless clearly specified to the contrary, such as via an explicit definition, assertion, or argument, with respect to any claim of any application claiming priority hereto, and whether originally presented or otherwise: (i) there is no requirement for the inclusion of any particular described or illustrated characteristic, function, activity, or element, any particular sequence of activities, or any particular interrelationship of elements; (ii) any elements can be integrated, segregated, and/or duplicated; (iii) any activity can be repeated, any activity can be performed by multiple entities, and/or any activity can be performed in multiple jurisdictions; and (iv) any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim seeking priority hereto, then any such conflicting information in such incorporated by reference material is specifically not incorporated by reference herein.

Accordingly, the descriptions and drawings are to be regarded as illustrative in nature, and not as restrictive.

INDUSTRIAL APPLICABILITY

The invention relates to methods for depolymerizing cellulose or starch such that the cellulose or starch can be more easily hydrolyzed into sugars for fermentation into ethanol.

What is claimed is:

1. A method for depolymerizing polysaccharides, the method comprising:
   reacting polysaccharides having a first average molecular weight with hydroxyl free radicals to produce polysaccharides having a second average molecular weight lower than the first average molecular weight,
   wherein the hydroxyl free radicals are formed by interaction of an oxidant with a catalyst selected from the group consisting of iron methylglycine diacetate and iron-2,3,4,5,6 pentahydroxyhexanoate.

2. The method of claim 1 wherein:
   the oxidant is selected from the group consisting of peroxides, ozone, hypochlorites, persulfates, permanganates, peracetic acid, chlorine dioxide, chlorites, halogens, and mixtures thereof.

3. The method of claim 1 wherein:
   the oxidant is selected from the group consisting of hydrogen peroxide, calcium peroxide, magnesium peroxide, and mixtures thereof.

4. The method of claim 1 wherein:
   the polysaccharides comprise starch.

5. The method of claim 1 wherein:
the second average molecular weight is at least 50% lower than the first average molecular weight.

6. The method of claim 1 wherein:
the polysaccharides comprise cellulose, and
the oxidant is added at about 1% to about 10% by weight of the cellulose.

7. The method of claim 6 wherein:
the catalyst is added at an oxidant to catalyst weight ratio of about 1:2 to about 9:1.

8. The method of claim 1 wherein:
the pH is adjusted to 5.0 to 10.0.

9. The method of claim 1 wherein:
the polysaccharides are reacted at a pressure above atmospheric pressure.

10. A method for producing ethanol, the method comprising:
reacting polysaccharides having a first average molecular weight with hydroxyl free radicals to produce polysaccharides having a second average molecular weight lower than the first average molecular weight, the hydroxyl free radicals being formed by interaction of an oxidant with a catalyst selected from the group consisting of iron methylglycine diacetate and iron-2,3,4,5,6 pentahydroxyhexanoate;
hydrolyzing the polysaccharides having the second average molecular weight into at least one sugar; and
fermenting the sugar into ethanol.

11. The method of claim 10 wherein:
the polysaccharides comprise cellulose.

12. The method of claim 10 wherein:
the oxidant is selected from the group consisting of peroxides, ozone, hypochlorites, persulfates, permanganates, peracetic acid, chlorine dioxide, chlorites, halogens, and mixtures thereof.

13. The method of claim 10 wherein:
the oxidant is selected from the group consisting of hydrogen peroxide, calcium peroxide, magnesium peroxide, and mixtures thereof.

14. The method of claim 10 wherein:
the catalyst is added at an oxidant to catalyst weight ratio of about 1:2 to about 9:1.

15. A method for producing glucose, the method comprising:
providing a material including starch or cellulose;
contacting the material with hydroxyl free radicals formed by interaction of an oxidant with a catalyst selected from the group consisting of iron methylglycine diacetate and iron-2,3,4,5,6 pentahydroxyhexanoate, and
hydrolyzing the material to produce glucose.

16. The method of claim 15 wherein:
the material comprises cellulose.

17. The method of claim 15 wherein:
the oxidant is selected from the group consisting of peroxides, ozone, hypochlorites, persulfates, permanganates, peracetic acid, chlorine dioxide, chlorites, halogens, and mixtures thereof.

* * * * *